United States Patent
Horita (10) Patent No.: US 8,040,561 B2
(45) Date of Patent: Oct. 18, 2011

(54) METHOD AND SYSTEM FOR PREDICTING PRINT COLORS

(75) Inventor: Shuhei Horita, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 598 days.

(21) Appl. No.: 12/132,725

(22) Filed: Jun. 4, 2008

(65) Prior Publication Data

US 2009/0021807 A1  Jan. 22, 2009

(30) Foreign Application Priority Data

Jul. 17, 2007 (JP) ................................ 2007-185820

(51) Int. Cl.
*H04N 1/52* (2006.01)
*H04N 1/60* (2006.01)
(52) U.S. Cl. .......... 358/1.9; 358/504; 358/518; 358/534
(58) Field of Classification Search .................... 358/1.9, 358/504, 518, 534; 356/402, 407, 408; 382/112, 382/162, 167; 347/19; 101/484
See application file for complete search history.

(56) References Cited

U.S. PATENT DOCUMENTS

| | | | |
|---|---|---|---|
| 5,357,448 A * | 10/1994 | Stanford | 382/112 |
| 7,423,778 B2 * | 9/2008 | Hersch et al. | 358/1.9 |
| 7,474,784 B2 | 1/2009 | Hasegawa | |
| 7,552,988 B2 * | 6/2009 | Yamamoto et al. | 347/19 |
| 2002/0131770 A1 | 9/2002 | Meier et al. | |
| 2005/0111017 A1 | 5/2005 | Takahashi et al. | |
| 2005/0219593 A1 | 10/2005 | Hoshino | |
| 2007/0157840 A1* | 7/2007 | Mayer | 101/484 |
| 2009/0080009 A1 | 3/2009 | Takahashi et al. | |

FOREIGN PATENT DOCUMENTS

| | | |
|---|---|---|
| JP | 08-178752 A | 7/1996 |
| JP | 2000-346706 A | 12/2000 |
| JP | 2002-098590 A | 4/2002 |
| JP | 2002-243548 A | 8/2002 |
| JP | 2002-305666 A | 10/2002 |
| JP | 2004-064546 A | 2/2004 |
| JP | 2005-184116 A | 7/2005 |
| JP | 2005-294976 A | 10/2005 |
| JP | 2006-121124 A | 5/2006 |
| JP | 2007-043286 A | 2/2007 |

OTHER PUBLICATIONS

Rejection of the Application, dated May 10, 2011, issued in corresponding JP Application No. 2007-185820, 3 pages in English and Japanese.

* cited by examiner

*Primary Examiner* — Scott A Rogers
(74) *Attorney, Agent, or Firm* — Sughrue Mion, PLLC (57) ABSTRACT

Inherent reflectances and scattering coefficients of color materials to be used in producing a print are calculated, and target printing base solid predicted reflectances are calculated using the calculated inherent reflectances and scattering coefficients, and the spectral reflectance of a target printing base, according to the Kubelka-Munk theory. Colorimetric values are calculated from the target printing base solid predicted reflectances. Differences are determined between calculated target printing base solid predicted colorimetric values and standard printing base solid calorimetric values obtained from a color chart, whereupon target printing base halftone differential predicted calorimetric values are calculated from the determined differences. The target printing base halftone differential predicted colorimetric values and standard printing base halftone colorimetric values of the color chart are added, and a print predicting profile is generated.

10 Claims, 9 Drawing Sheets

METHOD AND SYSTEM FOR PREDICTING PRINT COLORS

BACKGROUND OF THE INVENTION

1. Field of the Invention

The present invention relates to a method and system for predicting the print colors of a print produced by a printing press.

2. Description of the Related Art

Prints are produced by generating original film plates in various colors including cyan (C), magenta (M), yellow (Y), and black (K), for example, producing PS plates (presensitized plates) from the original film plates by exposure and development, mounting the PS plates on a printing press such as a rotary press or the like, and adjusting various printing conditions, including printing pressure, dampening water, temperature, etc.

Therefore, complex steps are involved in producing prints. In order to produce a print in desired colors, it has been customary, prior to the production of the print, to generate a proof sheet using a simple output device such as a color printer or the like, and then to confirm the generated proof sheet and adjust the printing conditions.

Since the colors of prints differ depending on the physical properties of the printing bases (printing sheets) and color materials (printing inks) used to produce the prints, it is necessary to generate a proof sheet while taking into account the combinations of such printing bases and color materials.

According to the related art disclosed in Japanese Laid-Open Patent Publication No. 2006-121124, a certain number of color patches are printed on a target printing base and the color patches are calorimetrically measured, whereby a profile for generating a proof sheet for the prints to be printed using a reference printing base is corrected based on the colorimetric values.

The disclosed process requires a large expenditure of time and labor for correcting the profile, because a number of color patches are required to be printed on the target printing base and colorimetrically measured each time the target printing base and the color materials are changed.

SUMMARY OF THE INVENTION

It is a general object of the present invention to provide a method and system for predicting the print colors of a print easily and highly accurately, with respect to a target printing base and the color materials used to produce the print, without the need for forming a color chart on the printing base or for calorimetrically measuring the color chart.

A major object of the present invention is to provide a method and system for predicting the print colors of a print according to desired color materials on a target printing base, using colorimetric values obtained from a color chart produced on a standard printing base using the desired color materials.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
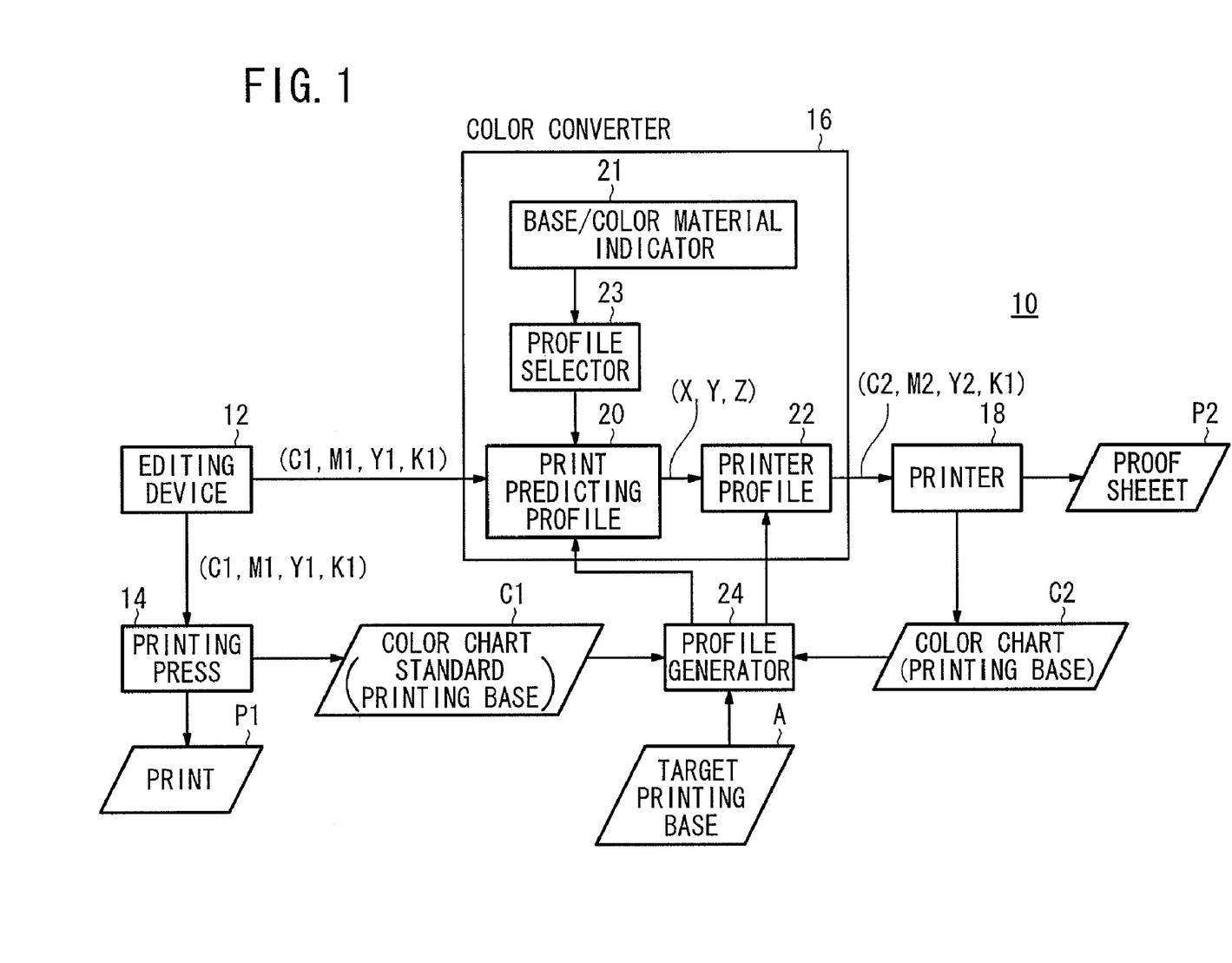
FIG. 1 is a block diagram of an overall arrangement of a print color predicting system according to an embodiment of the present invention.

FIG. 1 shows in block form a print color predicting system 10 according to an embodiment of the present invention. As shown in FIG. 1, the print color predicting system 10 comprises an editing device 12 for editing CMYK image data (C1, M1, Y1, K1) for controlling C, M, Y and K colors, a printing press 14 for producing a print P1 based on the edited CMYK image data (C1, M1, Y1, K1), a color converter 16 for converting the CMYK image data (C1, M1, Y1, K1) into CMYK image data (C2, M2, Y2, K2) for predicted colors, a printer 18 for generating a proof sheet P2 for a print P1 based on the CMYK image data (C2, M2, Y2, K2), and a profile generator 24 for generating a print predicting profile 20 and a printer profile 22, which are incorporated into the color converter 16. The color converter 16 includes a base/color material indicator 21 for indicating a target printing base (printing sheet) and color materials (printing inks) to be used in producing the print P1, and a profile selector 23 for selecting a print predicting profile 20 corresponding to the target printing base and the color materials that are indicated by the base/color material indicator 21.

The print predicting profile 20 is a profile for predicted device-independent colorimetric values (predicted colorimetric values) of the print P1 produced by the printing press 14, e.g., tristimulus values (X,Y, Z) of the print P. Specifically, the print predicting profile 20 for the print P1, which is produced using given color materials on a standard printing base forming a standard printing sheet, is generated based on existing CMYK image data (device-dependent data) and colorimetric values of a color chart C1, which is produced on the standard printing base from the CMYK image data by the printing press 14. A print predicting profile 20 for the print P1, which is produced using given color materials on a target printing base A forming a desired target printing sheet, is generated by correcting the print predicting profile 20 on the standard printing base, using the spectral reflectance of the target printing base A and the property values of the color materials.

The printer profile 22 is a profile for converting device-independent colorimetric values (predicted colorimetric values) of the print P1 predicted by the print predicting profile 20, e.g., tristimulus values (X,Y, Z) of the print P, into CMYK image data depending on the output characteristics of the printer 18. The printer profile 22 is generated based on existing CMYK image data and calorimetric values of a color chart C2, which is produced by the printer 18 on a printing base forming a printing sheet.

Figure 2:
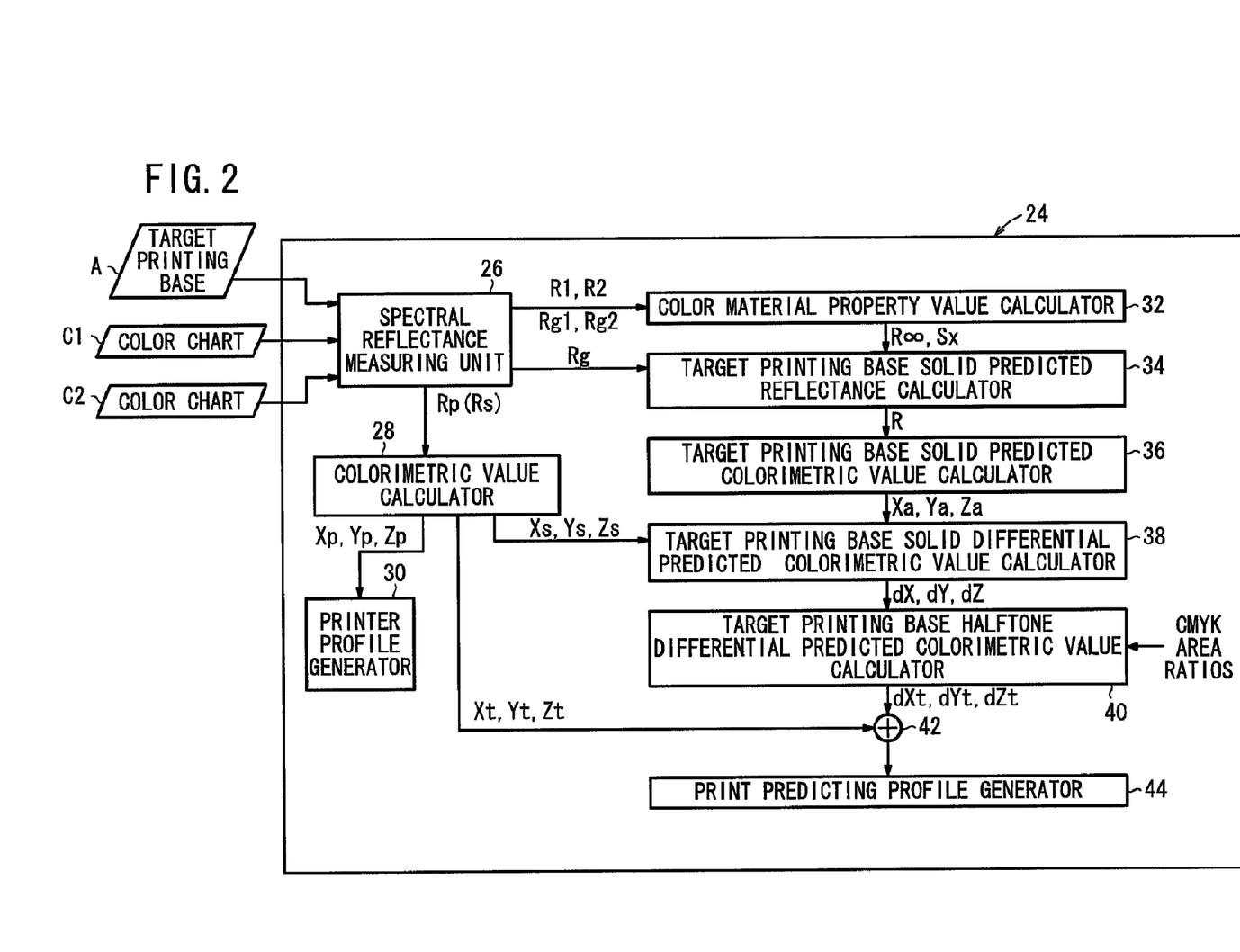
FIG. 2 is a block diagram of a profile generator of the print color predicting system shown in FIG. 1.

FIG. 2 shows an arrangement of the profile generator 24. As shown in FIG. 2, the profile generator 24 includes a spectral reflectance measuring unit 26 for measuring spectral reflectances of the target printing base A and the color charts C1, C2, a calorimetric value calculator 28 for calculating calorimetric values from the measured spectral reflectances, and a printer profile generator 30 for generating the printer profile 22 from the calorimetric values of the color chart C2 produced by the printer 18.

The profile generator 24 also includes a color material property value calculator 32 for calculating inherent reflectances and scattering coefficients, which represent property values of the color materials, using the spectral reflectances of the color chart C1 and the standard printing base, a target printing base solid predicted reflectance calculator 34 for calculating predicted spectral reflectances of single colors and superposed colors of the color materials, whose halftone dot percentage (%) on the target printing base A is 100% (solid), using the spectral reflectance of the target printing base A and the property values of the color materials, a target printing base solid predicted colorimetric value calculator 36 for calculating predicted calorimetric values from the predicted spectral reflectances, a target printing base solid differential predicted colorimetric value calculator 38 for calculating differences of the predicted colorimetric values with respect to the single colors and superposed colors of the solid color materials on the target printing base A, using the colorimetric values of the color chart C1 calculated by the calorimetric value calculator 28 and the predicted colorimetric values, a target printing base halftone differential predicted calorimetric value calculator 40 for calculating halftone differential predicted colorimetric values, which represent differences of the predicted colorimetric values with respect to arbitrary area ratios of the colors C, Y, M, K using the differences of the predicted calorimetric values, an adder 42 for adding the colorimetric values of the color chart C1 calculated by the colorimetric value calculator 28 and the halftone differential predicted colorimetric values on the target printing base A as calculated by the target printing base halftone differential predicted calorimetric value calculator 40, and a print predicting profile generator 44 for generating a print predicting profile 20 using predicted calorimetric values that are produced as the sum of the calorimetric values and the halftone differential predicted colorimetric values added by the adder 42.

The print color predicting system 10 according to the embodiment of the present invention is basically constructed as described above. A method of predicting print colors, which is carried out by the print color predicting system 10, shall be described below.

Figure 3:
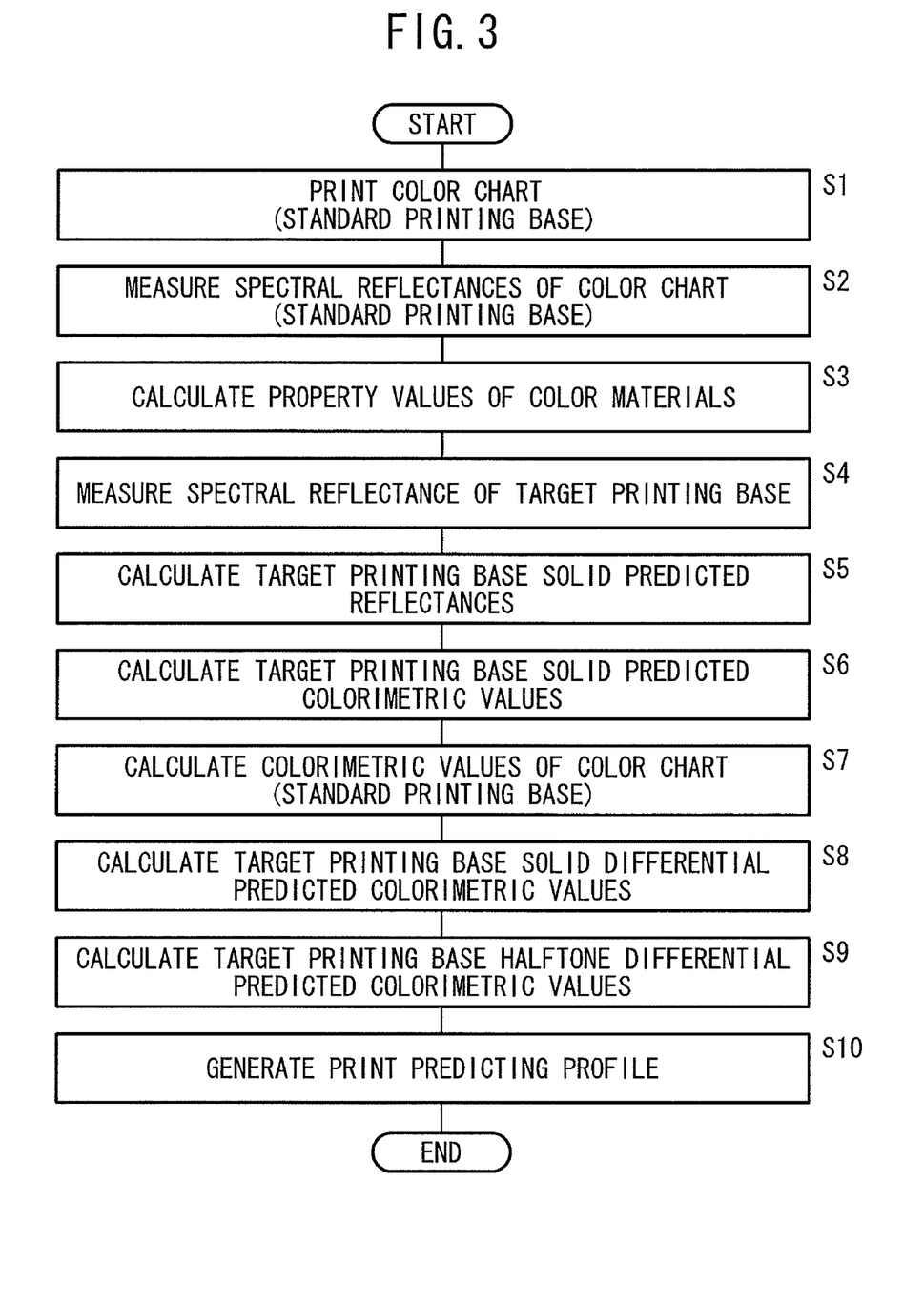
FIG. 3 is a flowchart of a sequence of generating a print predicting profile.

First, a sequence for generating a print predicting profile 20 that is performed by the profile generator 24 shall be described below with reference to FIG. 3.

The editing device 12 supplies known CMYK image data to the printing press 14, which prints a color chart C1 with given color materials on a standard printing base (step S1). The color chart C1 comprises a number of color patches, e.g., about 1000 color patches, printed in respective halftone dot percentages (%) of the CMYK image data at predetermined intervals in the range from 0% to 100%.

Then, the spectral reflectance measuring unit 26 measures the spectral reflectances of the color patches on the color chart C1 generated in step S1 as well as on the standard printing base (step S2).

The color material property value calculator 32 calculates inherent reflectances and scattering coefficients, which represent property values of the color materials C, M, Y, K, using the measured spectral reflectances of the color chart C1 and the standard printing base (step S3).

Figure 4:
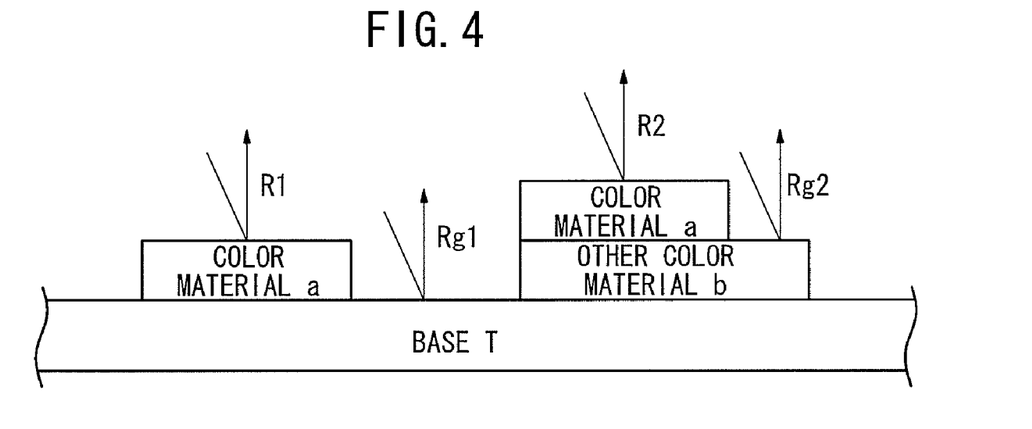
FIG. 4 is a view illustrative of a process for calculating color material property values.

Calculation of the inherent reflectances and scattering coefficients in step S3 shall be described in greater detail below. In FIG. 4, a base T made of an opaque material has a spectral reflectance Rg1, a color material "a" printed on the base T has a spectral reflectance R1, a color material "b" printed on the base T has a spectral reflectance Rg2, and the color material "a" printed on the base T with the color material "b" interposed therebetween has a spectral reflectance R2 (R1>R2). An inherent reflectance R∞, which represents the spectral reflectance assuming the color material "a" has an infinite thickness, is expressed by:

$$R\infty = \{C + \sqrt{(C^2 - 4)}\}/2 \qquad (1)$$

where, $$C = \{(R1+Rg2)(R2 \cdot Rg1-1)-(R2+Rg1)(R1 \cdot Rg2-1)\}/(R2 \cdot Rg1 - R1 \cdot Rg2) \qquad (2)$$

(See, Special Topic: "'It's only paper, yet it's paper, and it's paper after all'—Properties of Paper, Methods of Evaluating Them, and Standardization Trends", Journal of Japan Image Society, Vol. 150, 2004.) If R1<R2, then the suffixes "1" and "2" in equation (2) are switched.

The spectral reflectance Rg1 can be obtained by measuring the spectral reflectance of the standard printing base with the color chart C1 printed thereon, whereas the spectral reflectances R1, R2, Rg2 can be obtained by measuring the spectral reflectances of corresponding color patches of the single colors and superposed colors whose halftone dot percentage (%) is 100% (solid). The spectral reflectance Rg1 is not limited to being the spectral reflectance of the standard printing base, but may also be obtained as a spectral reflectance from an arbitrary printing base.

Figure 5:
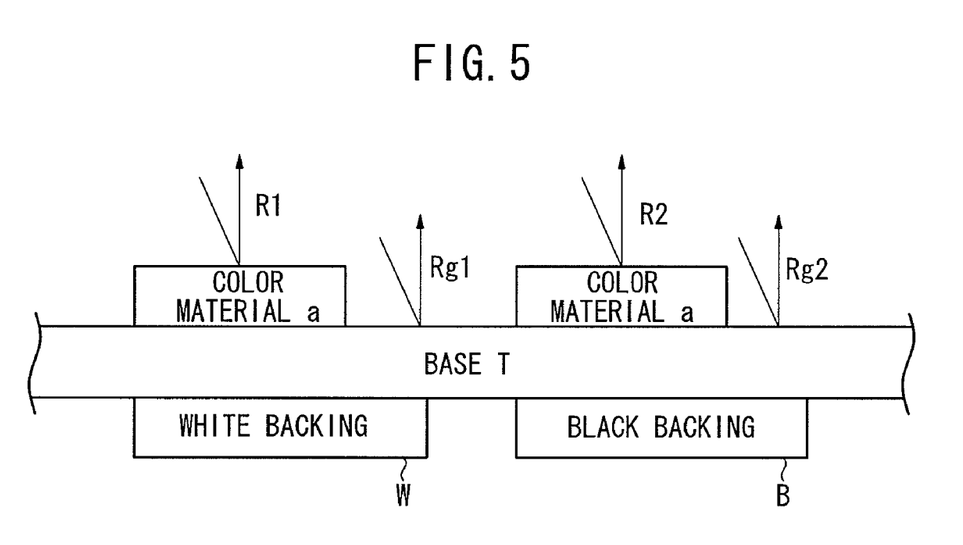
FIG. 5 is a view illustrative of a process for calculating color material property values.

If the base T is transparent or semitransparent, then as shown in FIG. 5, the inherent reflectance R∞ may be determined by the above equation (1) from the spectral reflectances R1, Rg1 of the color material "a" and a base T which is lined with a white backing W, and the spectral reflectances R2, Rg2 of the color material "a" and a base T which is lined with a black backing B. If the color material "a" can be made sufficiently thick, then the inherent reflectance R∞ may be directly measured.

Assuming the film thickness of a color material is represented by x, then the scattering coefficient S of the color material is expressed by:

$$S \cdot x = \ln[\{(R\infty - Rgn)(1/R\infty - Rn)\}/\{(R\infty - Rn)(1/R\infty - Rgn)\}]/(1/R\infty - R\infty) \qquad (3)$$

where Rn represents R1 or R2 and Rgn represents Rg1 or Rg2. (See, "Basics and Applied Technologies of Color Representation", page 88, equation (21) (Trikeps).) Since it is difficult to measure the film thickness x, Sx is regarded as Sx=S·x, wherein Sx is the scattering coefficient of the color material having a film thickness of X.

The inherent reflectances R∞ and scattering coefficients Sx of the color materials C, M, Y, K are determined in the manner described above.

After the spectral reflectance Rg of an arbitrary target printing base A is measured by the spectral reflectance measuring unit 26 (step S4), the target printing base solid predicted reflectance calculator 34 calculates target printing base solid predicted reflectances R using the spectral reflectance Rg of the target printing base A along with the inherent reflectances R∞ and scattering coefficients Sx of the color materials, which have been calculated by the color material property value calculator 32, as follows (step S5):

$$R=[(Rg-R\infty)/R\infty-R\infty(Rg-1/R\infty)\exp\{Sx(1/R\infty-R\infty)\}]/ \\ [(Rg-R\infty)-(Rg-1/R\infty)\exp\{Sx(1/R\infty-R\infty)\}] \quad (4)$$

Equation (4) is the Kubelka-Munk equation, using the inherent reflectances R∞ and scattering coefficients Sx of the color materials. (See, P. Kubelka, "New Contributions to the Optics of Intensely Light-Scattering Materials. Part 1," J. Opt. Soc. Am. 38, 448 (1948).)

Figure 6:
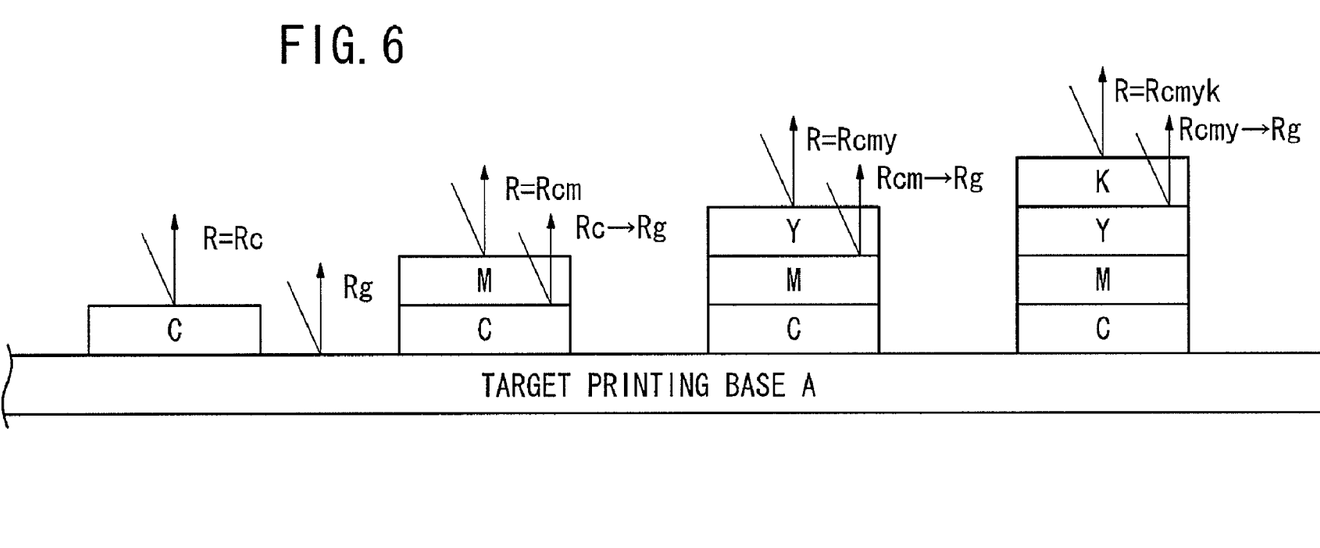
FIG. 6 is a view illustrative of a process for calculating a target printing base solid predicted reflectance.

As shown in FIG. 6, the target printing base solid predicted reflectances of the color materials C, M, Y, K according to equation (4) refer to the spectral reflectances of the solid colors C, M, Y, K on the target printing base A (in FIG. 6, the single color C is illustrated with its spectral reflectance R=Rc) and the spectral reflectances of the superposed solid colors C, M, Y, K on the target printing base A (in FIG. 6, the superposed colors C, M, the superposed colors C, M, Y, and the superposed colors C, M, Y, K are illustrated with their respective combined spectral reflectances R=Rcm, Rcmy, Rcmyk). The spectral reflectance Rg represents the spectral reflectance directly below the uppermost color material.

The inherent reflectance R∞, the scattering coefficient S, and the absorption coefficient K are related to each other as follows:

$$K/S=(1-R\infty)^2/2R\infty \quad (5)$$

Therefore, the target printing base solid predicted reflectances R may be determined by the Kubelka-Munk equation, represented by the following equation (6) based on any two independent values of the above property values, e.g., the scattering coefficients S (Sx) and absorption coefficients K of the color materials:

$$R=[1-Rg\{a-b\cdot\coth(b\cdot Sx)\}]/\{a+b\cdot\coth(b\cdot Sx)-Rg\} \quad (6)$$

where,
$a=(S+K)/S$;
$b=\sqrt{(a^2-1)}$; and
$\coth(t)=(e^t+e^{-t})/(e^t-e^{-t})$ The target printing base solid predicted colorimetric value calculator 36 calculates the target printing base solid predicted colorimetric values Xa, Ya, Za as predicted values from the target printing base solid predicted reflectances R calculated by the target printing base solid predicted reflectance calculator 34 (step S6). The target printing base solid predicted colorimetric values Xa, Ya, Za include target printing base calorimetric values calculated from the spectral reflectance Rg measured from the target printing base A.

The colorimetric value calculator 28 calculates the standard printing base solid colorimetric values Xs, Ys, Zs as measured values from the spectral reflectances of solid single color patches of C, M, Y, K along with color patches produced by superposing these solid single color patches, among the spectral reflectances Rs of the color chart C1 on the standard printing base, which are measured by the spectral reflectance measuring unit 26 (step S7). The standard printing base solid calorimetric values Xs, Ys, Zs include standard printing base colorimetric values calculated from the spectral reflectance Rs of the standard printing base.

The target printing base solid differential predicted calorimetric value calculator 38 calculates target printing base solid differential predicted colorimetric values dX, dY, dZ, as differences between the target printing base solid predicted colorimetric values Xa, Ya, Za calculated by the target printing base solid predicted colorimetric value calculator 36 and the standard printing base solid calorimetric values Xs, Ys, Zs calculated by the colorimetric value calculator 28, with respect to the solid single colors C, M, Y, K and the colors produced by superposing these single colors, according to the following equations (7), (8) and (9) (step S8):

$$dX=Xa-Xs \quad (7)$$

$$dY=Ya-Ys \quad (8)$$

$$dZ=Za-Zs \quad (9)$$

Then, the target printing base halftone differential predicted colorimetric value calculator 40 calculates target printing base halftone differential predicted colorimetric values dXt, dYt, dZt, with respect to halftones of C, M, Y, K on the target printing base A, by distributing the target printing base solid differential predicted colorimetric values dX, dY, dZ calculated by the target printing base solid differential predicted colorimetric value calculator 38, depending on the area ratios of C, M, Y, K (step S9).

The target printing base halftone differential predicted colorimetric values dXt, dYt, dZt may be determined by the Neugebauer equation, as represented by equation (10) below. Although equation (10) is applied to represent three colors C, M, Y for illustrative purposes, this equation also is applicable to four colors C, M, Y, K or five or more colors. In equation (10), dXw represents the difference between the target printing base colorimetric value Xa and the standard printing base colorimetric value Xx, while dXc, dXm, dXy represent the differences of the solid single color patches of C, M, Y. Further, dXcm, etc., represent the differences of the color patches produced by superposing the solid single colors C, M, Y. The same holds true for the other colorimetric values Y, Z. The values c, m, y represent the area ratios of C, M, Y. The target printing base halftone differential predicted colorimetric values dXt, dYt, dZt, which represent halftone differences, may be obtained by varying the values of c, m, y by 0.1 between 0 and 1.

$$\begin{pmatrix} dXt \\ dYt \\ dZt \end{pmatrix} = \begin{bmatrix} dXw & dXc & dXm & dXy & dXcm & dXmy & dXcy & dXcmy \\ dYw & dYc & dYm & dYy & dYcm & dYmy & dYcy & dYcmy \\ dZw & dZc & dZm & dZy & dZcm & dZmy & dZcy & dZcmy \end{bmatrix} \quad (10)$$

$$\begin{bmatrix} (1-c)(1-m)(1-y) \\ c(1-m)(1-y) \\ m(1-y)(1-c) \\ y(1-c)(1-m) \\ c\cdot m(1-y) \\ m\cdot y(1-c) \\ y\cdot c(1-m) \\ c\cdot m\cdot y \end{bmatrix}$$

The target printing base halftone differential predicted calorimetric values dXt, dYt, dZt thus calculated are added in the adder 42 to the standard printing base halftone colorimetric values Xt, Yt, Zt calculated by the colorimetric value calculator 28 from the spectral reflectances of the color patches of the color chart C1, thereby calculating target printing base halftone predicted colorimetric values X, Y, Z as follows:

$$X=Xt+dXt \quad (11)$$

$$Y=Yt+dYt \quad (12)$$

$$Z=Zt+dZt \quad (13)$$

Then, the print predicting profile generator 44 generates a print predicting profile 20 representing the relationship between the CMYK image data from which the color chart C1 has been generated and the target printing base halftone predicted calorimetric values X, Y, Z (step S10).

The generated print predicting profile 20 is set in the color converter 16. The print predicting profile 20 may be generated depending on a combination of the target printing base A and the color materials used, whereupon the print predicting profile 20 is set in the color converter 16.

Figure 7:
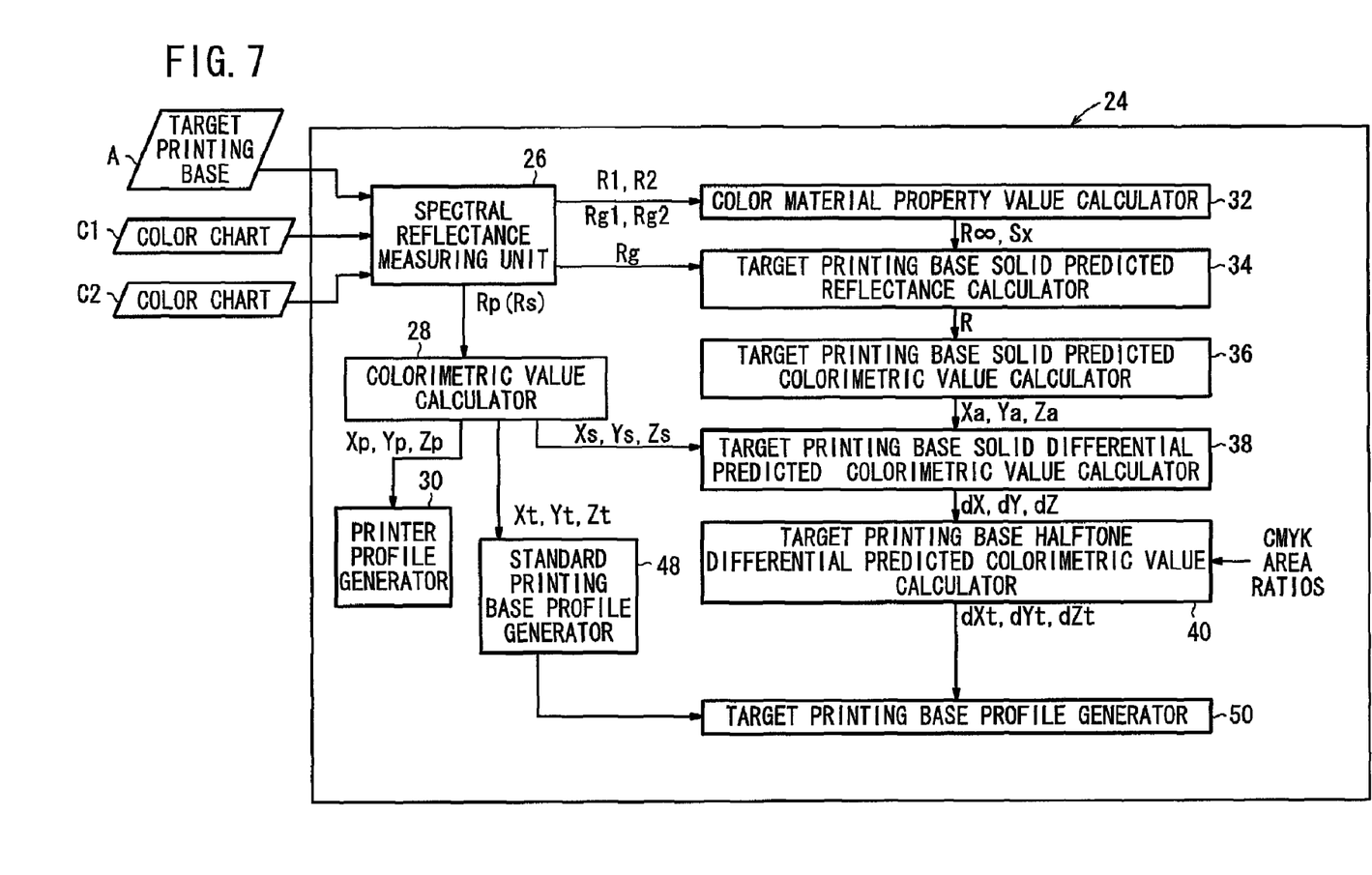
FIG. 7 is a block diagram of a profile generator according to another embodiment of the present invention.

In the above description, the target printing base halftone predicted colorimetric values X, Y, Z are calculated, and the print predicting profile 20 is generated using the calculated target printing base halftone predicted colorimetric values X, Y, Z. However, as shown in FIG. 7, a standard printing base profile generator 48 may also generate a standard printing base profile based on the measured values of the color chart C1 produced on the standard printing base, wherein a target printing base profile generator 50 adds the target printing base halftone differential predicted colorimetric values dXt, dYt, dZt calculated by the target printing base halftone differential predicted calorimetric value calculator 40 to the standard printing base halftone calorimetric values Xt, Yt, Zt of the standard printing base profile, thereby generating a print predicting profile 20 with respect to the desired target printing base A.

Figure 8:
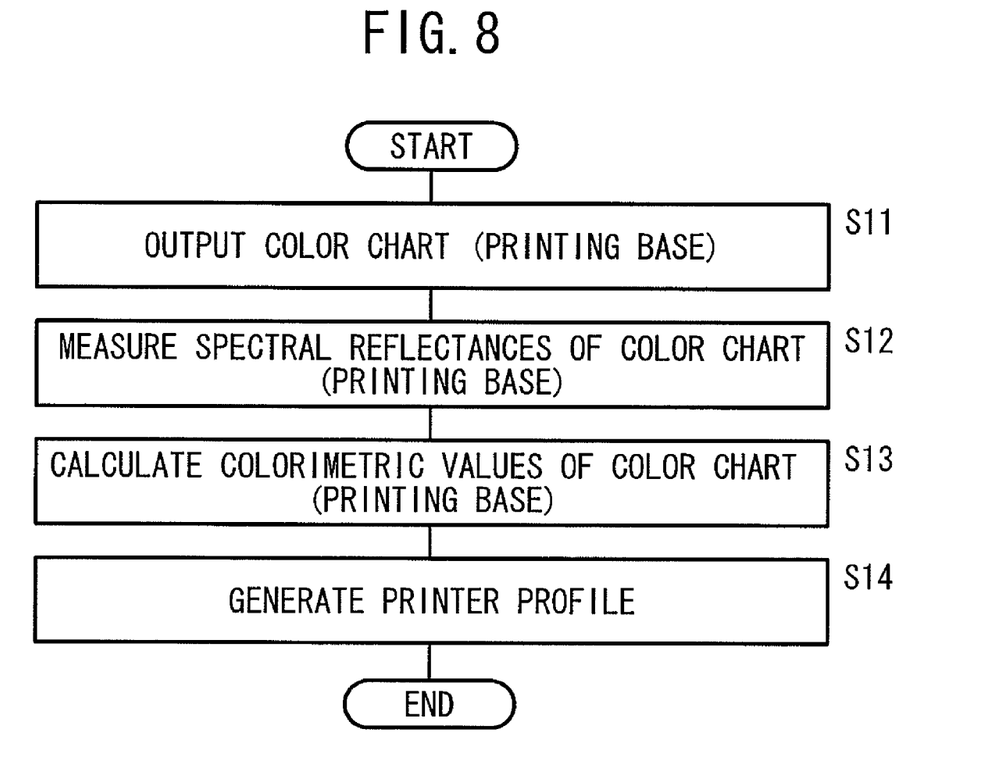
FIG. 8 is a flowchart of a sequence of generating a printer profile.

A sequence for generating a printer profile 22 that is performed by the profile generator 24 shall be described below with reference to FIG. 8.

The color converter 16 supplies known CMYK image data to the printer 18, which outputs a color chart C2 made up of a plurality of color patches on a printing base (step S11), in the same manner used when printing the color chart (step S1).

Then, the spectral reflectance measuring unit 26 measures the color patches of the color chart C2 to produce spectral reflectances Rp (step S12), and the colorimetric value calculator 28 calculates tristimulus values (X, Y, Z), for example, from the measured spectral reflectances Rp (step S13). The printer profile generator 30 generates a printer profile 22 representing the relationship between the tristimulus values (X, Y, Z) and the CMYK image data used to generate the color chart C2 (step S14). The generated printer profile 22 is set in the color converter 16.

After the print predicting profile 20 and the printer profile 22, which correspond to the target printing base A and the color materials, have thus been set in the color converter 16, a proof sheet P2 for a print P1 to be obtained from desired CMYK image data (C1, M1, Y1, K1) is generated.

Figure 9:
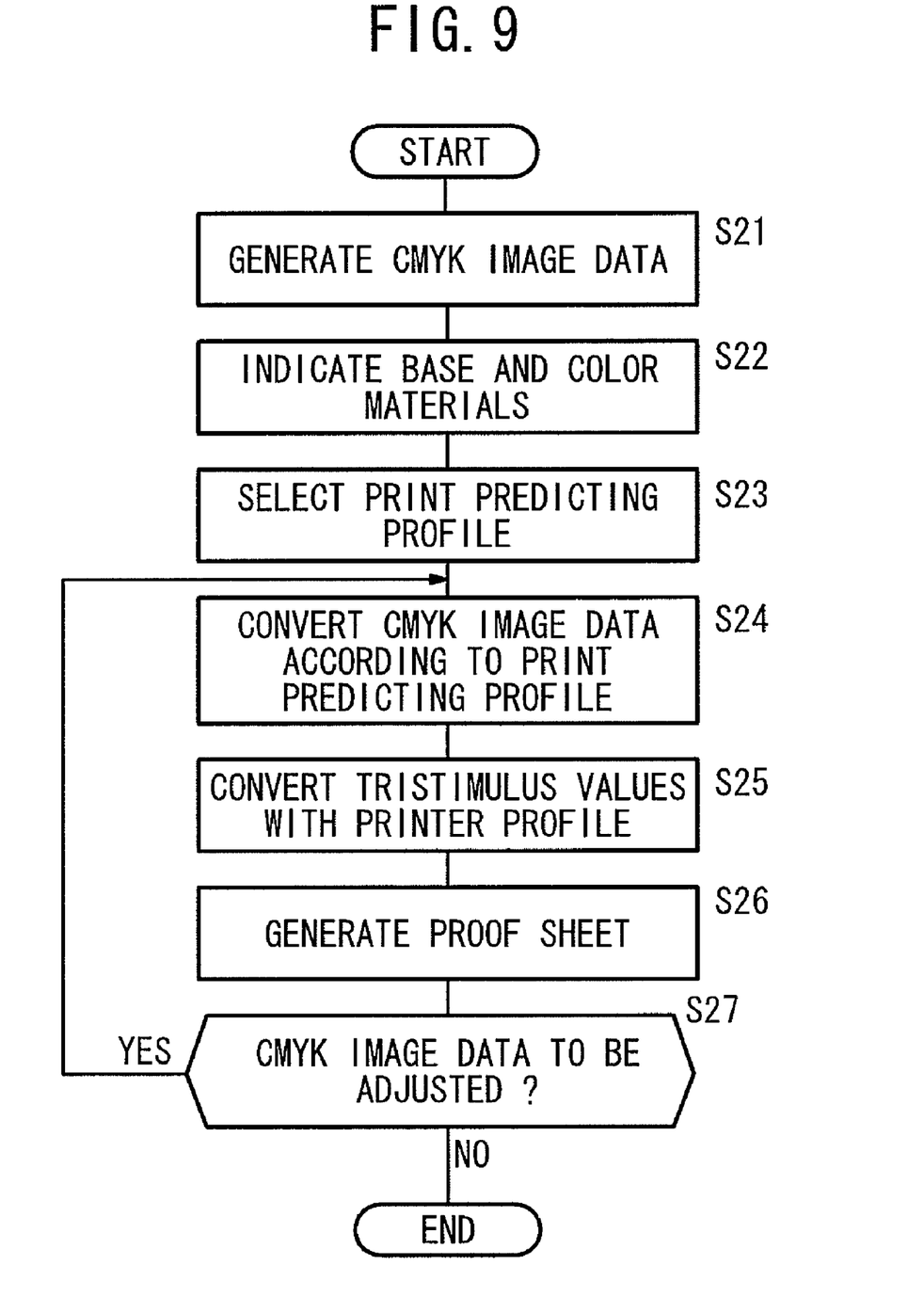
FIG. 9 is a flowchart of a sequence for generating a proof sheet.

A sequence for generating a proof sheet P1 shall be described below with reference to FIG. 9.

The editing device 12 generates desired CMYK image data (C1, M1, Y1, K1) (step S12) and supplies the generated CMYK image data (C1, M1, Y1, K1) to the color converter 16. In the color converter 16, the base/color material indicator 21 indicates a target printing base and color materials to be used by the printing press 14 (step S22), while the profile selector 23 selects a print predicting profile 20 corresponding to the target printing base and the color materials that are indicated by the base/color material indicator 21 (step S23).

Then, using the selected print predicting profile 20, the color converter 16 converts the CMYK image data (C1, M1, Y1, K1), which are device-dependent data, into tristimulus values (X, Y, Z), which are device-independent data (step S24).

Next, the tristimulus values (X, Y, Z) are converted by the printer profile 22 into CMYK image data (C2, M2, Y2, K2) depending on the output characteristics of the printer 18 (step S25). Using the CMYK image data (C2, M2, Y2, K2), the printer 18 generates a proof sheet P2 (step S26).

The operator confirms the proof sheet P2. If necessary, the operator adjusts the CMYK image data (C1, M1, Y1, K1), and repeats the process to generate another proof sheet P2 (step S27). When the desired proof sheet P2 is obtained, the operator supplies the CMYK image data (C1, M1, Y1, K1) to the printing press 14, which generates the print P1.

In the above embodiment, the color converter 16 determines tristimulus values (X, Y, Z) from the CMYK image data (C1, M1, Y1, K1) using the print predicting profile 20, and thereafter determines the CMYK image data (C2, M2, Y2, K2) from the tristimulus values (X, Y, Z) using the printer profile 22. However, the color converter 16 may also determine CMYK image data (C2, M2, Y2, K2) from the CMYK image data (C1, M1, Y1, K1), via colorimetric values $L^*$, $a^*$, $b^*$ rather than tristimulus values (X, Y, Z).

The print predicting profile 20 and the printer profile 22 may be combined into a single profile, and the color converter 16 may determine CMYK image data (C2, M2, Y2, K2) from the CMYK image data (C1, M1, Y1, K1) using the single profile.

In the print color predicting system 10, the proof sheet P2 is generated by the printer 18. However, the proof sheet P2 may also be displayed on a color monitor, rather than being generated by the printer 18. If the proof sheet P2 is displayed on a color monitor, the profile generator 24 generates a monitor profile by colorimetrically measuring the color chart C2 displayed on the color monitor, and then sets the monitor profile in the color converter 16.

The print color predicting system 10 is not limited to a system that generates a profile for device-dependent data in four C, M, Y, K colors, but also is applicable to a system for generating a print predicting profile 20 for device-dependent data in any number of colors, i.e., two or more colors.

Although certain preferred embodiments of the present invention have been shown and described in detail, it should be understood that various changes and modifications may be made to the embodiments without departing from the scope of the invention as set forth in the appended claims.

What is claimed is:

1. A method of predicting colors of a print produced by a printing press, comprising the step of:

with a calculating device predicted colorimetric values of a solid print to be produced on a target printing base with color materials, based on a spectral reflectance of said target printing base and property values of said color materials, said solid print having a combination of area ratios of 0% and 100%;

determining differences between measured colorimetric values of a solid color chart produced on a standard printing base with said color materials and having a combination of area ratios of 0% and 100%, and said predicted colorimetric values; and predicting colors of a print to be produced on said target printing base with said color materials and having an arbitrary area ratio, based on said differences.

2. A method according to claim 1, wherein said property values comprise two independent property values from among inherent reflectances, scattering coefficients, and absorption coefficients of said color materials.

3. A method according to claim 1, further comprising the step of:

adding adjusted differences produced by adjusting said differences depending on said arbitrary area ratio, to the measured colorimetric values of said color chart produced on said standard printing base with said color materials and having a predetermined area ratio, thereby to calculate predicted calorimetric values of the print to be produced on said target printing base with said color materials and having said arbitrary area ratio.

4. A method according to claim 1, wherein the colors of the print to be produced on said target printing base with said color materials are predicted based on a Kubelka-Munk equation.

5. A method according to claim 3, wherein said adjusted differences depending on said arbitrary area ratio are adjusted based on a Neugebauer equation.

6. A method according to claim 1, further comprising the steps of:
setting a standard printing base profile representing the relationship between measured calorimetric values of said color chart produced on said standard printing base with said color materials and having a predetermined area ratio, and said area ratio; and
correcting said standard printing base profile according to said differences so as to generate a target printing base profile for said target printing base.

7. A system for predicting colors of a print produced by a printing press, comprising:
a solid predicted colorimetric value calculating device for calculating predicted colorimetric values of a solid print to be produced on a target printing base with color materials and having a combination of area ratios of 0% and 100%, based on a spectral reflectance of said target printing base and property values of said color materials;
a solid difference calculating device for calculating solid differences between measured colorimetric values of a solid color chart, produced on a standard printing base with said color materials and having a combination of area ratios of 0% and 100%, and said predicted colorimetric values;
a halftone differential calculating device for calculating halftone differences of a print produced on said target printing base with said color materials and having a halftone area ratio, based on said solid differences; and
a print predicting profile generating device for generating a print predicting profile for predicting colors of a print to be produced on said target printing base with said color materials, using the measured colorimetric values of said color chart produced on said standard printing base with said color materials and having a predetermined area ratio, and said halftone differences, whereby the colors of the print can be predicted using said print predicting profile.

8. A system according to claim 7, wherein said property values comprise two independent property values from among inherent reflectances, scattering coefficients, and absorption coefficients of said color materials.

9. A system for predicting colors of a print produced by a printing press, comprising:
a solid predicted colorimetric value calculating device for calculating predicted colorimetric values of a solid print to be produced on a target printing base with color materials and having a combination of area ratios of 0% and 100%, based on a spectral reflectance of said target printing base and property values of said color materials;
a solid difference calculating device for calculating solid differences between measured calorimetric values of a solid color chart, produced on a standard printing base with said color materials and having a combination of area ratios of 0% and 100%, and said predicted calorimetric values;
a halftone differential calculating device for calculating halftone differences of a print produced on said target printing base with said color materials and having a halftone area ratio, based on said solid differences;
a standard printing base profile generating device for generating a standard printing base profile representing the relationship of the measured colorimetric values with respect to said color chart produced on said standard printing base with said color materials and having a predetermined area ratio; and
a print predicting profile generating device for correcting said standard printing base profile with said halftone differences, so as to generate a print predicting profile for predicting colors of a print to be produced on said target printing base with said color materials, whereby the colors of the print can be predicted using said print predicting profile.

10. A system according to claim 9, wherein said property values comprise two independent property values from among inherent reflectances, scattering coefficients, and absorption coefficients of said color materials.

* * * * *